United States Patent [19]

Doner et al.

[11] Patent Number: 4,828,734
[45] Date of Patent: May 9, 1989

[54] GREASE COMPOSITIONS CONTAINING BORATED OXAZOLINE COMPOUNDS AND HYDROXY-CONTAINING SOAP THICKENERS

[75] Inventors: John P. Doner, Sewell; Andrew G. Horodysky, Cherry Hill; John A. Keller, Jr., Pitman, all of N.J.

[73] Assignee: Mobil Oil Corporation, New York, N.Y.

[21] Appl. No.: 54,121

[22] Filed: May 14, 1987

Related U.S. Application Data

[63] Continuation of Ser. No. 769,827, Aug. 27, 1985, abandoned.

[51] Int. Cl.$^4$ .......................................... C10M 113/16
[52] U.S. Cl. .................................. 252/49; 252/32.7 E; 252/49.6; 252/49.7
[58] Field of Search ...................... 252/49, 49.7, 49.6, 252/32.7 E

[56] References Cited

U.S. PATENT DOCUMENTS

| | | | |
|---|---|---|---|
| 2,053,474 | 9/1936 | Graves et al. | 260/98 |
| 2,397,956 | 4/1946 | Fraser | 252/40 |
| 2,703,784 | 3/1955 | Fields | 252/32.7 |
| 2,703,785 | 3/1955 | Roberts et al. | 252/33.4 |
| 2,813,830 | 11/1957 | Trautman | 252/49.6 |
| 2,815,325 | 12/1957 | Pohorilla et al. | 252/42.1 |
| 2,905,644 | 9/1959 | Butter | 252/51.5 R |
| 2,943,054 | 6/1960 | Worth | 252/40.7 |
| 2,975,134 | 3/1961 | Cook | 252/40.7 |
| 3,009,791 | 11/1961 | Emrick | 252/49.6 |
| 3,012,968 | 12/1961 | Emrick | 252/49.6 |
| 3,095,375 | 6/1963 | Pitman | 252/28 |
| 3,125,523 | 3/1964 | Siegart et al. | 252/33.6 |
| 3,125,524 | 3/1964 | Siegart et al. | 252/33.6 |
| 3,125,525 | 3/1964 | Siegart et al. | 252/33.6 |
| 3,158,574 | 11/1964 | Greenwood et al. | 252/36 |
| 3,224,971 | 12/1965 | Knowles et al. | 252/46.3 |
| 3,361,672 | 1/1968 | Andress et al. | 252/49.6 |
| 3,446,808 | 5/1969 | Cyba | 252/49.6 |
| 3,625,899 | 12/1971 | Sawyer | 252/75 |
| 3,697,574 | 10/1972 | Piasek | 260/462 R |
| 3,704,308 | 11/1972 | Piasek et al. | 260/462 R |
| 3,711,411 | 1/1973 | Sawyer et al. | 252/78 |
| 3,711,412 | 1/1973 | Sawyer et al. | 252/78 |
| 3,736,357 | 5/1973 | Piasek et al. | 260/570.5 P |
| 3,751,365 | 8/1973 | Piasek et al. | 252/49.6 |
| 3,758,407 | 9/1973 | Harting | 252/18 |
| 3,923,712 | 12/1975 | Vickery | 260/28.5 B |
| 4,016,092 | 4/1977 | Andress | 252/32.5 |
| 4,071,548 | 1/1978 | Okamoto | 252/49.6 |
| 4,097,389 | 6/1978 | Andress, Jr. | 252/49.6 |
| 4,140,492 | 2/1979 | Feldman et al. | 44/62 |
| 4,159,957 | 7/1979 | deVries | 252/33.4 |
| 4,182,823 | 1/1980 | Schoenberg | 526/298 |
| 4,244,829 | 1/1981 | Coupland et al. | 252/56 R |
| 4,317,739 | 3/1982 | Spence | 252/47.5 |
| 4,328,113 | 5/1982 | Horodysky et al. | 252/49.6 |
| 4,370,248 | 1/1983 | Horodysky et al. | 252/49.6 |
| 4,374,032 | 2/1983 | Gemmill et al. | 252/49.6 |
| 4,376,712 | 3/1983 | Horodysky et al. | 252/49.6 |
| 4,382,006 | 5/1983 | Horodysky | 252/49.6 |
| 4,389,322 | 6/1983 | Horodysky | 252/49.6 |
| 4,394,278 | 7/1983 | Horodysky et al. | 252/46.3 |
| 4,402,842 | 9/1983 | Horodysky et al. | 252/47.5 |
| 4,406,802 | 9/1983 | Horodysky et al. | 252/49.6 |
| 4,410,438 | 10/1983 | Horodysky | 252/49.6 |
| 4,426,305 | 1/1984 | Malec | 252/49.6 |
| 4,440,656 | 4/1984 | Horodysky | 252/49.6 |
| 4,472,289 | 9/1984 | Horodysky et al. | 252/49.6 |
| 4,486,321 | 12/1984 | Horodysky et al. | 252/46.3 |
| 4,524,005 | 6/1985 | Horodysky | 252/49.6 |
| 4,529,529 | 7/1985 | Horodysky | 252/49.6 |
| 4,582,617 | 4/1986 | Doner et al. | 252/32.7 |

FOREIGN PATENT DOCUMENTS

| | | |
|---|---|---|
| 711234 | 6/1965 | Canada . |
| 0067002 | 12/1982 | European Pat. Off. . |
| 0075478 | 3/1983 | European Pat. Off. . |
| 0134063 | 3/1985 | European Pat. Off. . |
| 1400020 | 7/1975 | United Kingdom . |
| 2102023 | 1/1983 | United Kingdom . |
| 2103651 | 2/1983 | United Kingdom . |
| 2106133 | 4/1983 | United Kingdom . |
| 2107734 | 5/1983 | United Kingdom . |
| 2125431 | 3/1984 | United Kingdom . |

OTHER PUBLICATIONS

C. J. Boner, "Manufacture and Application of Lubricating Greases", 1954, pp. 435–437, 497–498, 157.
C. V. Smalheer & R. K. Smith, "Lubricant Additives", 1967, Section I, pp. 1–11, Chapter 1.
G. G. Hawley, "The Condensed Chemical Dictionary", Ninth Edition, pp. 520 and 938.

Primary Examiner—Dixon, Jr. William R.
Assistant Examiner—Margaret B. Medley
Attorney, Agent, or Firm—Alexander J. McKillop; Charles J. Speciale; Van D. Harrison, Jr.

[57] ABSTRACT

Disclosed is a grease composition comprising a major proportion of a grease, a hydroxy-containing soap thickener and a minor amount of a boronated oxazoline compound. The hydroxy-containing soap thickener and boronated oxazoline compound are each added in amounts sufficient to increase the dropping point of the grease an appreciable amount. Generally this can be an increase of at least 15° F. and could be as great as 200° F. to 250° F. or more. Sulfur and phosphorus compounds can also be incorporated into the composition.

15 Claims, No Drawings

GREASE COMPOSITIONS CONTAINING BORATED OXAZOLINE COMPOUNDS AND HYDROXY-CONTAINING SOAP THICKENERS

This is a continuation of copending application Ser. No. 769,827, filed on Aug. 27, 1985 now abandoned.

BACKGROUND OF THE INVENTION

1. Nature of the Invention:

The invention is concerned with grease compositions. More particularly it is concerned with a grease composition comprising oil, hydroxy-containing soap thickener and certain borated oxazoline compounds and, optionally, phosphorus and sulfur moieties.

2. Prior Art:

U.S. Pat. No. 4,374,032 corresponding to application Ser. No. 134,849, filed Mar. 28, 1980, discloses the use of borated adducts of oxazolines as a component of lubricating oils. U.S. Pat. No. 4,374,032 is incorporated herein by reference.

The publication "Manufacture and Application of Lubricating Grease" by C. J. Boner (Reinhold Publishing Company) 1954, pp. 155 and 436, 437 disclose the use of lithium soaps in grease making. The publication "Lubricant Additive" by C. V. Smalheer et al (Leyuis-Hiles Co.) 1967, pp. 1–11, discloses the use of phosphonates and thiophosphonates as additives in lubricants. "Condensed Chemical Dictionary" 9th Edition, (Van Nostrand Reinhold Company) at pages 520 and 938 discloses the use of lithium hydroxystearate in grease making and zinc dialkyldithiophosphate as a lube oil additive.

These references, the publications by Boner and by Smalheer et al, and the "Condensed Chemical Dictionary" reference are incorporated herein by reference.

SUMMARY OF THE INVENTION

In accordance with this invention, there is provided an improved grease composition comprising a major proportion of a grease, a hydroxy-containing soap thickener and a minor amount of a boronated oxazoline compound. The hydroxy-containing soap thickener and boronated oxazoline compound are each added in amounts sufficient to increase the dropping point of the grease an appreciable amount. Generally this can be an increase of at least 15° F. and could be as great as 200° F. to 250° F. or more.

The Borated Oxazoline Compounds

The oxazoline compounds used in this invention are believed to have the following generalized structure

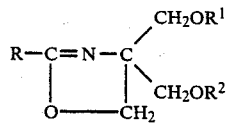

and

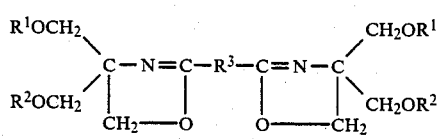

where R and $R^3$ are hydrocarbyl or hydrocarbylene groups of one to fifty carbon atoms and optionally contain sulfur, oxygen, nitrogen, or halogen. Preferably R and $R^3$ are of eight to twenty carbon atoms. $R^1$ and $R^2$ can be the same or different and can be hydrogen or have the generalized structure

where $R^4$ is hydrogen or a hydrocarbyl group of one to fifty carbon atoms. Preferably, at least one of $R^1$ or $R^2$ is hydrogen available for boration.

More particularly, the product can be made by reacting molar amounts or more than molar amounts of a carboxylic acid of the formula

with a hydroxyl amine such as tris(hydroxymethyl)aminomethane such that the oxazoline formed has the formula

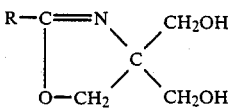

wherein R is as defined above, followed by reacting the oxazoline with an appropriate boronating agent including, but not limited to, boric acid, boron oxide, metaborate or a borate of the formula

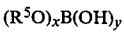

wherein $R^5$ is a $C_1$–$C_6$ alkyl group; x is 1 to 3, y is 1–3 and x+y=3. Boration can be partial or complete, or a large excess of boronating agent can be used, but for maximum effect, higher levels of borate are generally preferred.

The carboxylic acid, as indicated, may have from 10 to 50 carbon atoms, including the carboxyl carbon atom. These include the saturated decanoic, dodecanoic, tetradecanoic, octadecanoic, eicosanoic acids and the like, as well as the unsaturated acids, including particularly oleic acid.

The first reaction, i.e. between the monocarboxylic acid and the amine, can be carried out at from about 80° C. to about 250° C., preferably from about 120° C. to about 190° C. The temperature chosen will depend for the most part on the reactants chosen and whether or not a solvent is used. In carrying out this reaction, it is essential that quantities of reactants be chosen such that at least 1 and preferably 2 hydroxyls remain for the reaction with the boron compound. For example, in the reaction illustrated, one mole of the acid and one mole of the amine are required. A slight excess of amine may be used if desired, but an excess of acid in this case would lead to the formation of some monoester oxazoline, in addition to the preferred oxazoline. Mixtures of oxazolines can also be used.

In carrying out the reaction to form the boron product, up to stoichiometric amounts of the oxazoline and boron compound may be used. That is to say, boration can be partial or complete. An excess of borating agent can be used up to a 1000 percent excess. The temperature of this reaction can be from about 50° C. to about 300° C., preferably from about 70° C. to about 230° C.

While atmospheric pressure is generally preferred, the reaction with the boron compound can be advantageously run at from about 0.3 to about 2 atmospheres. Furthermore, a solvent is desirable. In general, any polar or non-polar solvent can be used including toluene, xylene, 1,4-dioxane or more polar reactive solvents, such as butanol-1 and pentanol, and the like.

The times for the reactions are not critical. Thus, any phase of the process can be carried out in from 1 to 48 hours. Other details for making the borated oxazoline compounds are set forth in U.S. Pat. No. 4,374,032.

A narrow class of thickening agents is used to make the grease of this invention. The thickening agents contain at least a portion of alkali metal, alkaline earth metal or amine soaps of hydroxyl-containing fatty acids, fatty glycerides and fatty esters such as methyl esters having from 12 to about 30 carbon atoms per molecule. The metals are typified by sodium, lithium, calcium and barium. Preferred is lithium. Preferred members among these acids and fatty materials are 12-hydroxystearic acid and glycerides and methyl esters containing 12-hydroxystearates, 14-hydroxystearic acid, 16-hydroxystearic acid and 6-hydroxystearic acid.

The entire amount of thickener need not be derived from the aforementioned members. Significant benefit can be attained using as little thereof as about 5 to 15 percent by weight of the total thickener and up to 100 percent of the total thickener. A complementary amount, i.e., up to about 85% by weight of a wide variety of thickening agents can be used in the grease of this invention. Included among the other useful thickening agents are alkali and alkaline earth metal soaps of methyl-12-hydroxystearate, diesters of a $C_4$ to $C_{12}$ dicarboxylic acid and tall oil fatty acids. Other alkali or alkaline earth metal fatty acids containing from 12 to 30 carbon atoms and no free hydroxyl may be used. These include soaps of stearic and oleic acids.

Greases benefiting from the borated additive can be produced by any of the commonly used manufacturing techniques which include open or closed kettle saponification. Saponifications can also be carried out in pressure vessels, commonly known as contactors, at a variety of temperature and pressures. Continuous grease production type equipment can also be used to produce the grease which will be treated with the borated additive. Operating temperatures and pressures are variable as with the conditions normally used to carry out the saponification for the type of reactants involved; but the temperatures generally range from room temperature 25° C. to 232° C. and pressures as high as 190 psig and as low as vacuum.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline, as well as certain hydrophobic clays. These thickening agents can be prepared from clays which are initially hydrophilic in character, but which have been converted into a hydrophobic condition by the introduction of long-chain hydrocarbon radicals into the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. These methods of grease manufacture, being well known to those skilled in the art, is believed to require no further discussion, and does not form a part of the present invention.

The third member(s) that may be present in the grease composition are the phosphorus and sulfur moieties. Both of these can be present in the same molecule, such as in a metal or non-metal phosphorodithioate of the formula

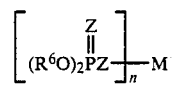

wherein $R^6$ is a hydrocarbyl qroup containinq 3 to 18 carbon atoms or mixtures thereof. $R^6$ can also be a hydroxyl-containinq or ester-containing hydrocarbyl qroup or may additionally contain sulfur. M is preferably a metal, but may be a non-metal, such as one of those mentioned hereinbelow, n is the valence of M and Z is oxygen or sulfur, at least one Z being sulfur. The phosphorodithioate can also be derived from diols such as 1,2 dodecanediol, 1,3 pentanediol and similar $C_4$-$C_{20}$ diols and mixtures. The phosphorodithioate can also be complexed as a zinc acetate complexed zinc phosphorodithioate.

In this compound, $R^6$ is preferably an alkyl qroup and may be a propyl, butyl, pentyl, hexyl, octyl, decyl, dodecyl, tetradecyl or octadecyl qroup, includinq those derived from isopropanol, propanol, butanol, isobutanol, sec-butanol, 4-methyl-2-pentanol, 2-ethylhexanol, oleyl alcohol, and mixtures thereof. Further included are alkaryl groups such as butylphenyl, octylphenyl, nonylphenyl and dodecylphenyl groups.

The metals embraced by M include those in Groups IA, IIA, IIB, and VIII of the Periodic Table. Some that may be mentioned are lithium, sodium, calcium, zinc, cadmium, silver, gold and molybdenum. Non-metallic ions include organic groups derived from vinyl esters such as vinyl acetate, vinyl ethers such as butyl vinyl ether and epoxides such as propylene oxide and 1,2-epoxydodecane. The non-metallic ions may also be derived from nitrogenous compounds such as those derived from hydrocarbyl amines and diamines, including oleylamine and N-oleyl-1,3-propylenediamine and such as the imidazolines and oxazolines.

The phosphorus and sulfur can also be supplied from the combination of two separate compounds, such as the combination of (1) a dihydrocarbyl phosphite having 2 to 10 carbon atoms in each hydrocarbyl group or mixtures of phosphites and (2) a sulfide such as sulfurized isobutylene, dibenzyl disulfide, sulfurized terpenes, phosphorodithionyl disulfide and sulfurized jojoba oil. The phosphites include the dibutyl, dihexyl, dioctyl, didecyl and similar phosphites. Phosphate esters containing 4 to 20 carbon atoms in each hydrocarbyl group, such as tributyl phosphate, tridecyl phosphate, tricresyl phosphate and mixtures of such phosphates, can also be used. Compounds containing both sulfur and phosphorus can be used, such as phosphorodithionyl disulfide.

In summary, it is essential to the practice of this invention, in which greases having improved dropping points are obtained, that at least the borated friction reducing compounds and the hydroxy-containing thickener be included in the grease composition. Thus: first, with respect to the preparation of the grease, the thickener will have at least about 15% by weight of a metal or non-metal hydroxyl-containing soap therein, the total thickener being from about 3 percent to about 20 percent by weight of the grease composition;

second, there will be added to the grease from about 0.1 percent to about 10 percent by weight, preferably about 0.5 percent to about 2.0 percent of a borated oxazoline compound or mixture of borated oxazoline compounds, and as a third component optionally to provide further improvement, the composition may have therein from 0.2 percent to about 10 percent by weight, preferably from 1 percent to 2 percent by weight, of phosphorus- and sulfur-containing compounds or a mixture of two or more compounds which separately supply the phosphorus and sulfur moieties. If separate compounds are used, an amount of the mixture equivalent to the above concentration levels is used to supply desired amounts of phosphorus and sulfur.

Base oils used in the grease are mineral oil, synthetics, hydrocarbon fluids or mixtures of these. In addition, oxygen-containing fluids can be used such as dibasic acid esters, polyol esters, polyglycols, or phosphate esters. The alkyl benzene-type lubricants are also included. Other fluids that may be used are halogenated fluids, silicones, silicate esters, or polyphenyl ethers. These lubricant fluids can be mixed or used alone as the base oil portion of the grease. In general, mineral oils, both paraffinic, naphthenic and mixtures thereof, may be of any suitable lubricating viscosity range, as for example, from about 45 SSU at 100° F. to about 6000 SSU at 380° C. (100° F.), and preferably from about 50 to about 250 SSU at 99° C. (210° F.) These oils may have viscosity indexes ranging to about 100 or higher. Viscosity indexes from about 70 to about 95 are preferred. The average molecular weights of these oils may range from about 250 to about 800. In making the grease, the lubricating oil from which it is prepared is generally employed in an amount sufficient to balance the total grease composition, after accounting for the desired quantity of the thickening agent, and other additive components to be included in the grease formulation.

In instances where synthetic oils are desired, in preference to mineral oils, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

The metallic soap grease compositions containing one or more of the borated friction reducing compounds and hydroxy-containing soap thickeners and, optionally, one or more of the sulfur and phosphorus combinations described herein provide advantages in increased dropping point, improved grease consistency properties, antirust characteristics and potential antifatigue, antiwear and antioxidant benefits unavailable in any of the prior greases known to us. The grease of this invention is unique in that it can be preferably manufactured by the admixture of additive quantities of the borated oxazoline compounds to the fully formed soap grease after completion of saponification.

EXAMPLES

To demonstrate the improved dropping point achieved with the combination of a hydroxy bearing thickener and borated oxazoline compounds the following greases were prepared.

EXAMPLE A

Fully Formulated Lithium Hydroxystearate Grease

This example illustrates the preparation of a grease containing a hydroxy-bearing thickener and a phosphorus-sulfur compound, but lacking the borated oxazoline compound. This grease approximates a prior art or state of the art grease.

A lithium hydroxystearate grease thickener was prepared by a saponifying mixture containing 50 weight percent of 12-hydroxystearic acid in a mixture of the acid and the glycerine thereof with lithium hydroxide in a mineral oil vehicle at about 177° C. (351° F.) in a closed contactor. After the thickener had been depressured and dehydrated in an open kettle, sufficient mineral oil was added to reduce the thickener content to about 9.0%. After the grease had cooled to 99° C., a typical grease additive package, consisting of an amine antioxidant, phenolic antioxidant, metallic dithiophosphate (phosphorodithioate) sulfur-containing metal deactivator and nitrogen containing antitrust additives, was added. This produced a fully formulated hydroxyl-containing soap grease. The dropping point of this formulated grease was 202° C. (395° F.). The grease was tested for dropping point to compare it with greases formulated according to this invention.

EXAMPLE B

Lithium Hydroxystearate Base Grease

This example illustrates the preparation of a grease containing a hydroxy-bearing thickener but without any additive package of sulfur and phosphorus compounds. This grease approximates a prior art grease without additives.

A lithium hydroxystearate-thickened base grease was prepared as generally described for Example A. No additive package was added to the grease. After reduction of the thickener content to about 10%, the grease (without additives) was cooled and held for subsequent testing. The dropping point of this base grease was 202° C. (395° F.).

EXAMPLE C

Lithium Stearate/Palmitate-Thickened Base Grease

A lithium stearate/palmitate (50% stearate/50% palmitate) base grease not containing any hydroxyl groups in the soap thickeners was prepared for evaluation as generally described in Example B. The total thickener content was about 10%. The dropping point was 207° C. (404° F.).

The effect of blending in two percent of each of the boron compounds described below into the hydroxystearate thickened grease and into the nonhydroxyl-containing stearate/palmitate-thickened grease was tested by measuring the dropping point of the mixed greases. Other blends of the greases were also tested. The test data is summarized in the accompanying table. It will be noted that the combination of hydroxyl bearing thickener and borated compound results in a grease of greatly improved dropping point. The further addition of sulfur and phosphorus compounds acted also to further increase the dropping point.

EXAMPLE I

Preparation of Boronated Additives (a) Preparation of oxazoline borate compounds (heptadecenyl oxazoline monooleate borate).

This example, as well as Example (b), illustrate the preparation of oxazoline borate compounds used in the grease composition of this invention.

Approximately 1211.4 grams of tris(hydroxymethyl)aminomethane, 5649 grams of oleic acid, and 1000 ml xylene were charged to a 12 l glass reactor equipped with heater, agitator and Dean-Stark tube with condenser. The reactants were heated to 195° C. (383° F.) until water evolution (548 ml total) ceased. The solvent was removed by vacuum topping at 130°–140° C. (266°–284° F.) to yield hydroxyl-containing heptadecenyl oxazoline monooleate ester.

Approximately 4000 grams of the above oxazoline, 130.5 grams of boric acid and 200 grams of n-butanol were charged to a reactor equipped as above and heated to a temperature of 160°–170° C. (320°–338° F.) over a period of 16 hours until water evolution ceased. The crude product was vacuum topped at 160°–170° C. (320°–338° F.) and filtered through diatomaceous earth to form an oxazoline ester borate. The product was an amber colored fluid which became more viscous upon cooling.

(b) Heptadecenyl Oxazoline Borate.

Approximately 1400 grams of oleic acid, 70 grams of isostearic acid, 635 grams of tris(hydroxymethyl)aminomethane and 300 grams of xylene were charged to a reactor equipped as generally described in Example I(a). The reactants were heated to 180° C. (356° F.) until water evolution ceased and were then vacuum topped to remove solvent to form a mixed dihydroxymethyl hydrocarbyl oxazoline.

Approximately 150 grams of the above dihydroxymethyl oxazoline, 40 grams of boric acid and 100 grams of toluene were heated in a reactor equipped as described above to 160° C. (320° F.) until water evolution during azeotropic distillation ceased. The solvent was vacuum topped at 160° C. (320° F.) to remove solvent and filtered at 100°–110° C. (212°–230° F.) through diatomaceous earth to form an amber-colored oxazoline borate. The product contained approximately 4.9% boron.

TABLE

| Grease Composition | Borated Compound | % of Borated Compound in Composition | % of Zinc Dialkyl Thiophosphate | Dropping Point ASTM D 2265 |
| --- | --- | --- | --- | --- |
| Example A - | | 0 | 1.5 | 202° C. (395° F.) |
| Hydroxy-bearing thickener & phosphorus-sulfur compound | | | | |
| Example B - Hydroxy-bearing thickener. No added phosphorus or sulfur or other additives | | 0 | 0 | 202° C. (395° F.) |
| Example C - Lithium stearate/palmitate thickener. No hydroxy-bearing thickener or added sulfur or phosphorus compounds | | 0 | 0 | 207° C. (404° F.) |
| Example B-1 | heptadecenyl oxazoline monooleate borate (I-a) | 2% | 0 | 232° C. (449° F.) |
| Example B-2 | oxazoline borate (I-(b) | 2% | 0 | 267° C. (513° F.) |
| Example B-3 | oxazoline borate (I-(b) | 2% | 1.5% | 319° C. (607° F.) |
| Example C-1 | oxazoline borate (I-(b) | 2% | 0 | (201° C.) (393° F.) |

What is claimed is:

1. A grease composition comprising a lubricating component, between about 3 and about 20 percent by weight of a thickener containing at least 15 percent by weight of thickener of a hydroxy-containing thickener and between about 0.1 and about 10 percent by weight of the total composition of an additive for elevating the dropping point of a grease comprising a borated oxazoline compound.

2. The grease composition of claim 1 wherein said borated oxazoline compound is obtained by reacting an oxazoline of the generalized structure

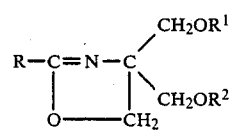

where R is a hydrocarbyl or hydrocarbylene group of one to fifty carbon atoms, at least one of $R^1$ or $R^2$ is hydrogen and the other is hydrogen or has the generalized structure

where $R^4$ is hydrogen or a hydrocarbyl group of one to fifty carbon atoms with boric acid, boron oxide, metaborate or a borate of the formula $(R^5O)_xB(OH)_y$ wherein x is 1 to 3, y is 0 to 2, their sum being 3 and $R^5$ is an alkyl group containing 1 to 6 carbon atoms.

3. The composition of claim 2 wherein R additionally contains sulfur, oxygen, nitrogen or halogen.

4. The grease composition of claim 1 wherein said borated oxazoline compound is obtained by reacting an oxazoline of the generalized structure

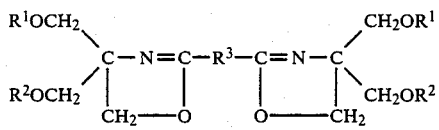

where $R^3$ is a hydrocarbyl or hydrocarbylene group of one to fifty carbon atoms, at least one of $R^1$ or $R^2$ is hydrogen and the other is hydrogen or has the generalized structure

where $R^4$ is hydrogen or a hydrocarbyl group of one to fifty carbon atoms with boric acid, boron oxide, metaborate or a borate of the formula

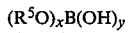

$(R^5O)_xB(OH)_y$ wherein x is 1 to 3, y is 0 to 2, their sum being 3 and $R^5$ is an alkyl group containing 1 to 6 carbon atoms.

5. The composition of claim 4 wherein R additionally contains sulfur, oxyqen, nitrogen or halogen.

6. The composition of claim 1 wherein said grease additionally contains between about 0.2 and about 10 percent by weight of phosphorus and sulfur containing compounds.

7. The composition of claim 1 wherein said borated oxazoline compound is the borated product of p-t-butyl-phenol obtained by reacting tris(hydroxymethyl)aminomethane and oleic acid.

8. The composition of claim 1 wherein said borated oxazoline compound is the borated reaction product obtained by reacting tris(hydroxymethyl)aminomethane and isostearic acid.

9. The composition of claim 1 wherein said hydroxy-containing thickener is lithium hydroxystearate.

10. The composition of claim 9 wherein said phosphorus and sulfur compound is zinc dihydrocarbyldithiophosphate.

11. A method for elevating the dropping point of a grease composition comprising incorporating into said grease: (1) between about 0.2 and about 10 percent by weight of the total composition of a borated oxazoline additive for elevating the dropping point of a grease and (2) between about 3 and about 20 percent by weight of the total composition of a thickener containing at least 15 percent by weight of a hydroxy-continuing soap thickener.

12. In a method for making grease wherein a liquid lubricant is mixed with a thickening agent, the improvement comprising adding to said grease between about 3 and about 20 percent by weight of a thickener containing at least 15 percent by weight of thickener of a hydroxy-containing thickener and between about 0.1 and about 10 percent by weight of the total composition of an additive for elevating the dropping point of a grease comprising a borated oxazoline compound.

13. The method of claim 11 additionally adding one or more compounds containing sulfur and phosphorus.

14. The composition of claim 1 wherein the lubricating component is mineral oil, synthetic oil, or a mixture thereof.

15. The composition of claim 14 wherein the synthetic oils are polyqlycols, synthetic hydrocarbons, alkyl benzenes, dibasic acid esters, polyol esters, phosphate esters or mixtures thereof.

* * * * *